US006860863B2

(12) United States Patent
Chow

(10) Patent No.: US 6,860,863 B2
(45) Date of Patent: Mar. 1, 2005

(54) CARPAL TUNNEL SPLINT FOR WEAR DURING NON-WORKING PERIODS

(76) Inventor: James C. Y. Chow, 4121 Veterans Memorial Dr., Mount Vernon, IL (US) 62864

( * ) Notice: Subject to any disclaimer, the term of this patent is extended or adjusted under 35 U.S.C. 154(b) by 345 days.

(21) Appl. No.: 10/086,154

(22) Filed: Feb. 26, 2002

(65) Prior Publication Data
US 2003/0163075 A1 Aug. 28, 2003

(51) Int. Cl.[7] ................................................. A41F 5/00
(52) U.S. Cl. ............................. 602/20; 602/21; 602/63; 602/75; 128/878
(58) Field of Search ............................. 602/20, 21, 63, 602/75, 22, 62, 64; 128/878, 879, 880; 2/16

(56) References Cited

U.S. PATENT DOCUMENTS

| 4,953,568 A | * | 9/1990 | Theisler ....................... 128/878 |
| 4,966,137 A | | 10/1990 | Davini |
| 4,996,979 A | * | 3/1991 | Grim et al. ..................... 602/21 |
| 5,279,545 A | * | 1/1994 | Reese, Sr. ..................... 602/21 |
| 5,417,645 A | | 5/1995 | Lemmen |
| 5,468,220 A | | 11/1995 | Sucher |
| 5,771,901 A | * | 6/1998 | O'Brien ....................... 128/878 |
| 6,106,492 A | | 8/2000 | Darcey |
| 6,120,472 A | | 9/2000 | Singer, Jr. |
| 6,213,969 B1 | | 4/2001 | MacMorran et al. |
| 6,341,376 B1 | * | 1/2002 | Smerdon, Jr. ..................... 2/16 |
| 6,482,168 B1 | * | 11/2002 | Betcher ....................... 602/21 |
| 6,517,501 B1 | * | 2/2003 | Slautterback ................ 602/20 |
| 6,561,995 B1 | * | 5/2003 | Thibodo, Jr. ................. 602/22 |

* cited by examiner

Primary Examiner—Fadi H. Dahbour
(74) Attorney, Agent, or Firm—Polster, Lider Woodruff & Lucchesi, L.C.

(57) ABSTRACT

A splint (10) worn by a sufferer of carpal tunnel syndrome. A first sleeve (12) fits over the person's hand (H) and extends up their arm (A) past their wrist (W). This sleeve is worn during non-working portions of the person's day and includes a support (14) formed in the palm portion of the sleeve to support the carpal tunnel and relieve pressure on the median nerve passing through it. This alleviates pain caused by carpal tunnel syndrome. A second sleeve (22) also fits over the person's hand and extends up their arm past their wrist. This second sleeve, which is also worn during non-working portions of the day, extends further up the person's arm than the first sleeve. A support (24) of this second sleeve extends along the back of the person's hand to also relieve pressure on the median nerve and alleviate the pain caused by carpal tunnel syndrome.

6 Claims, 2 Drawing Sheets ately to a splint worn on the hand and wrist by someone suffering from carpal tunnel syndrome. The splint is for use during non-working periods in which support of the wrist and treat the carpal tunnel syndrome.

CARPAL TUNNEL SPLINT FOR WEAR DURING NON-WORKING PERIODS

CROSS REFERENCE TO RELATED APPLICATIONS

STATEMENT REGARDING FEDERALLY SPONSORED RESEARCH OR DEVELOPMENT

BACKGROUND OF THE INVENTION

This invention relates to body supports, and more particularly to a splint worn on the hand and wrist by someone suffering from carpal tunnel syndrome. The splint is for use during non-working periods in which support of the wrist and treat the carpal tunnel syndrome.

Carpal tunnel syndrome is a condition resulting from a compression of the median nerve as it passes through the carpal tunnel portion of a person's wrist and hand. As shown in FIG. 1, the median nerve N carries sensations to and from a person's fingers F and powers movement of the person's thumb T. The nerve extends through the wrist W, and then has branches B extending to the fingers and thumb. A transverse carpal ligament L formed at the base of the hand H extends from one side of the hand, across the base of the palm of the hand, to the other side of the hand. The carpal tunnel T comprises a space in the center of the wrist through which extends the median nerve and flexor tendons for the hand. Carpal tunnel syndrome results from excessive pressure exerted on the median nerve typically resulting from constriction of the carpal tunnel. The resulting injury causes numbness in the wrist and hand at some times, and a tingling or burning sensation at others.

Treatment of a carpal tunnel injury often requires the sufferer to wear a splint to support the carpal tunnel and relieves the pressure on the nerve. Representative examples of such splints are shown, for example, in U.S. Pat. Nos. 6,213,969, 6,106,492, 6,120,472, 5,468,220, 5,417,645, and 4,966,137. The main purpose of these and other similar splints is to allow the wearer to perform those work related functions they are required to perform as part of their job, and which are often the cause of their injury in the first place.

While these splints are generally effective, they are primarily for use during the working portions of the person's day. Wearing the splint at other times has certain disadvantages. First, the type and degree of support needed in their working environment is not necessarily what is required, or preferred, at other times. Rather, during non-working times, a more neutral support that allows the wearer to perform a broader range of activities without discomfort is desirable. Second, many splints worn during working periods have straps, belts, or the like which secure the splint in place. However, if worn to bed, these straps and belts can scratch the wearer causing injury. Or, the wearer may subconsciously remove the splint, aggravating their injury. Third, in industrial settings, and even in some office environments, the splint worn during working hours can get very dirty because of the type of work the wearer does. Wearing the splint at other times can therefore be unsanitary as well as unsightly.

The carpal tunnel splint of the present invention is for use during times of the day other than work when support for the hand and wrist are still required, but not necessarily to the same degree as during work. Importantly, the splint allows the wearer to adjust the support provided the splint so that the splint accommodates those activities performed by the wearer during his or her non-working times and at bedtime.

BRIEF SUMMARY OF THE INVENTION

A carpal tunnel splint of the present invention includes a sleeve open at one end to fit over a person's hand and wrist. The other end of the sleeve has thumb and finger holes formed in it so the sleeve can be readily pulled on. The splint is worn during non-work periods and bedtime when the wearer needs a more neutral support that allows them to readily perform a wide range of activities. The support provided by the splint is adjustable to provide a level of comfort and support to the wearer which differs from that provided by the splint worn when the person is working. The splint is made of a lightweight material which fits easily underneath the person's clothing if so desired. When worn, the splint supports the wrist and relieves pressure on the median nerve. When the person goes to work, they replace the splint with one designed for the work they do. Other objects and features will be in part apparent and in part pointed out hereinafter.

BRIEF DESCRIPTION OF THE SEVERAL VIEWS OF THE DRAWINGS

The objects of the invention are achieved as set forth in the illustrative embodiments shown in the drawings which form a part of the specification.

Corresponding reference characters indicate corresponding parts throughout the several views of the drawings.

DETAILED DESCRIPTION OF INVENTION

Figures 1, 2:
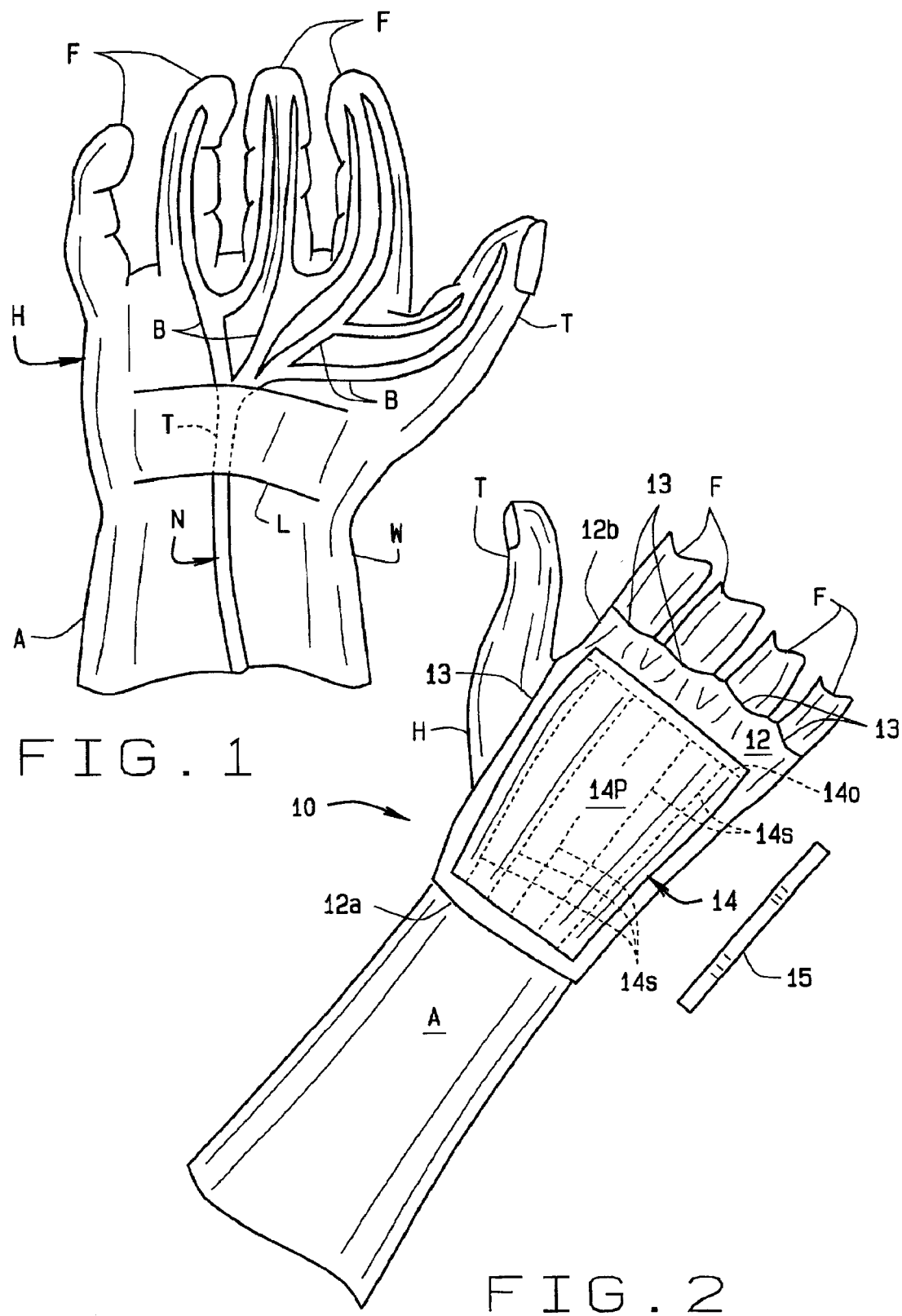
FIG. 1 is a simplified representation of a person's hand and wrist illustrating the median nerve whose branches extend to the fingers, the transverse carpal ligament, and the carpal tunnel.
FIG. 2 is a representation of a person's arm and wrist with a first embodiment of the splint of the present invention being worn by the person; and, FIG. 3 is a representation of the arm and wrist with a second embodiment of the splint being worn.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention. As various changes could be made in the above constructions without departing from the scope of the invention, it is intended that all matter contained in the above description or shown in the accompanying drawings shall be interpreted as illustrative and not in a limiting sense.

Referring to the drawings, a splint 10 of the present invention is for use in the treatment of carpal tunnel syndrome, the cause of which has been previously described. The splint of the present invention includes a sleeve 12 which over the person's hand H and extends up their arm A past their wrist W. Sleeve 12 is of a lightweight, elasticized, generally flesh colored material open at one end 12a, so to slide the sleeve up over the arm. The elastic material is a very light elastic so as not to increase pressure on the wrist. The other end 12b is closed except for finger holes 13 for the wearer's thumb and fingers. This allows the sleeve to be easily put on and comfortable to wear.

Sleeve 12 of splint 10 is to be worn primarily during the wearer's non-working hours. That is, splint 10 is worn in place of the splint worn by the person during his or her work periods. The sleeve includes a support means 14 incorporated into the sleeve and positioned to relieve pressure on the median nerve passing. This helps alleviate the pain caused by carpal tunnel syndrome. Importantly, the level of support is adjustable by the wearer so to provide the maximum amount of relief possible to him or her. Also, the type of support provided is more neutral than that provided by the splint worn at work. This is because the work splint is designed primarily to enable the wearer to perform work related tasks with as little discomfort as possible. However, the design of the work splint often inhibits many non-work related activities.

Means 14 includes a pocket 14p formed on the side of the sleeve 12 which fits over the person's palm. This pocket extends generally the length of the sleeve. A cushioning material fills the pocket, and this material is generally concentrated in the area of the transverse carpal ligament L. In a preferred embodiment of the invention, pocket 14p is an air pocket which is pressurized with air to a level which exerts an appropriate force on the wrist area so that the pain is alleviated. Alternately, pocket 14p comprises a series of slots 14s in which are inserted stiffeners 15. The stiffeners can be of a plastic or other lightweight material and are available with differing degrees of stiffness. The amount of support provided by splint 10 is therefore adjustable by the wearer. This is accomplished by controlling the amount of filler material, including the amount of air, with which the pocket is filled, or the amount of stiffness provided by the stiffeners 15 used by the wearer. Regardless of the support material employed, the amount of material, air pressure, or number and type of stiffeners are readily adjusted to increase or decrease the amount of support provided by the support means. With respect to amount of filler material or air, pocket 14p has an opening 140 at one end for adding or removing filler material, or increasing or decreasing the air pressure of the pocket. When stiffeners are used, there number and type are readily adjusted by the wearer to create the desired level of support.

Figure 3:
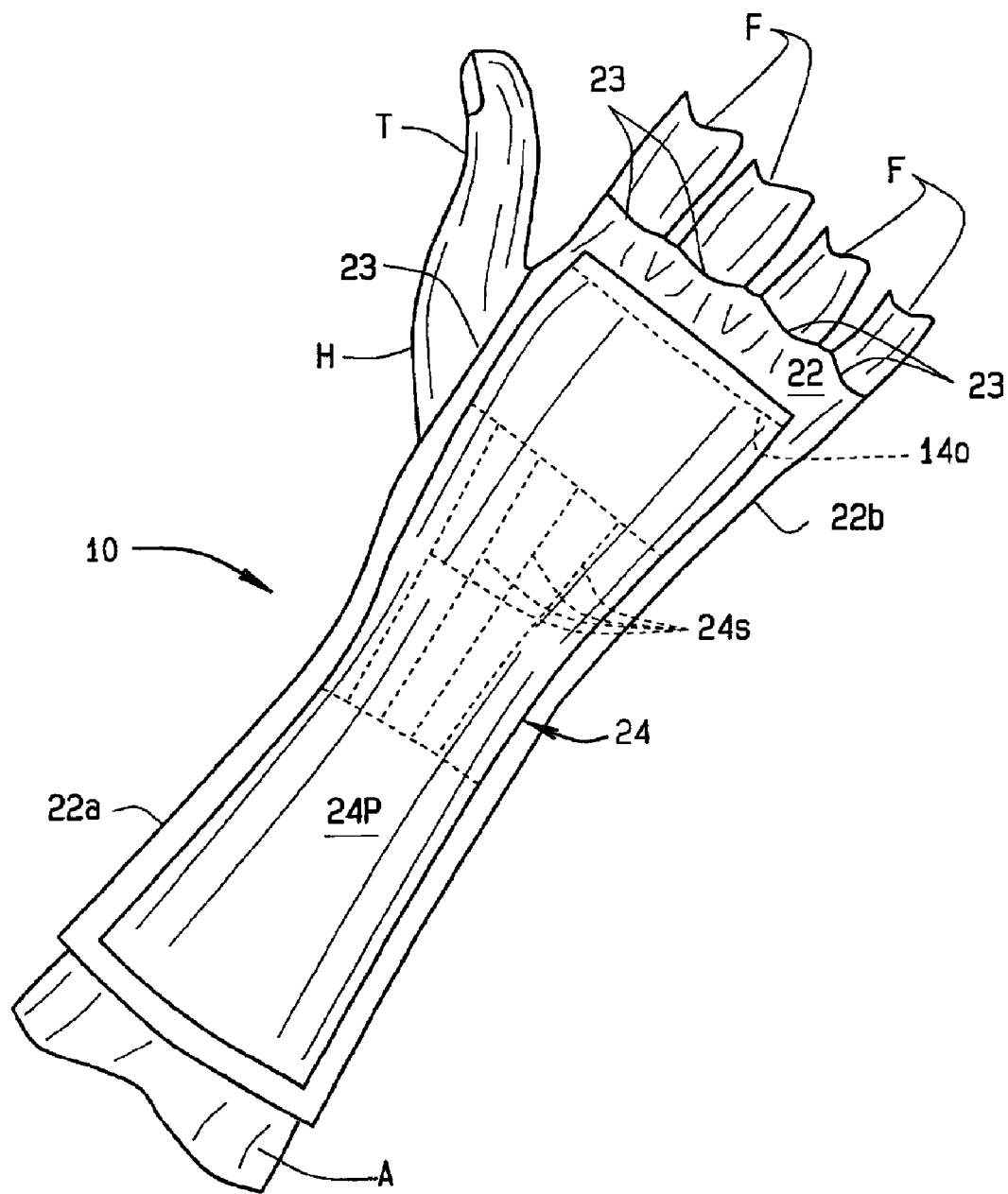

Splint 10 next includes a second sleeve 22 which also extends up the person's arm past their wrist. Sleeve 22, as shown in FIG. 3, extends further up the person's arm than sleeve 12. Sleeve 22 is also of a lightweight, elasticized, material which is open at one end 22a, so to slide the sleeve over the wearer's arm. The opposite end 22b of the sleeve is closed except for finger holes 23 for the wearer's thumb and fingers. As with sleeve 12, sleeve 22 is easy put on, comfortable to wear, and unobtrusive in appearance.

Sleeve 22 includes a support means 24. Unlike support means 14 of sleeve 12 which is generally in the palm of the hand, support means 24 extends along the back of the hand. However, like support means 14, support means 24 also supports the median nerve to alleviate pain caused by constriction of the carpal tunnel. Means 24 comprises a pocket 24p which, like pocket 14p, can be filled with a cushioning material, including air. While pocket 24p is shown to extend generally the length of the sleeve, it can be shorter. Also, the pocket can include slots 24s into which stiffeners such as the stiffener 15 can be inserted, and an opening 24o at one end for adjusting the amount of filler material or air in the pocket. Again, the wearer is able to adjust the amount of support provided by the splint to enable him or her to perform a wide range of non-work related activities without discomfort.

An advantage of splint 10 over other types of splints is that the splint, regardless of which type is worn, has no straps or belts. When worn during sleep, the person will not scratch or hurt themselves if they rub the splint up against the side of their face. The splint material is also washable in soap and water so it is easily kept clean. That is often not possible with splints worn during work. Finally, because the amount of support provided by the splint is adjustable, the wearer can increase the amount of support needed to perform certain activities comfortably, or decrease it if desired, by themselves. They therefore do not need to have more than one splint, nor do they need to visit their doctor or therapist every time they feel they need to adjust the amount of support provided by the splint.

In view of the above, it will be seen that the several objects and advantages of the present invention have been achieved and other advantageous results have been obtained.

Having thus described the invention, what is claimed and desired to be secured by Letters Patent is:

1. A splint worn by someone suffering from carpal tunnel syndrome during periods of time when the wearer is not engaging in activities which might aggravate their injury but still requires a level of support comprising:

a first sleeve fitting over the person's hand and extending up the person's arm past their wrist and including a first support means incorporated in the first sleeve and positioned to support the median nerve passing through the carpal tunnel and alleviate the pain caused by carpal tunnel syndrome; and a second sleeve extending up the person's arm past their wrist, the second sleeve extending further up the person's arm than the first splint sleeve, and a second support means incorporated in the second sleeve to also relieve pressure on the median nerve and further alleviate the pain caused by carpal tunnel syndrome, each sleeve being open at one end and closed at its opposite end, the open end of each sleeve being sized to fit over the person's arm and the opposite end having openings in it for the person's thumb and fingers so the respective sleeves can be fitted onto the person's arm.

2. The splint of claim 1 wherein each sleeve is of an elasticized material so to provide a snug fit when worn.

3. The splint of claim 1 wherein each support means includes a pocket formed adjacent an inner end of the respective sleeve and extending over the portion of the person's hand and wrist where the carpal tunnel extends.

4. The splint of claim 3 in which the pocket is filled with a support material for supporting the median nerve.

5. The splint of claim 4 in which the pocket is an air pocket pressurized with air to provide the requisite.

6. The splint of claim 4 further including a splint inserted into the pocket to support the medium nerve.

* * * * *